(12) United States Patent
Sandstrom et al.

(10) Patent No.: US 8,781,201 B2
(45) Date of Patent: Jul. 15, 2014

(54) METHOD OF OPERATING A PATHOLOGY LABORATORY

(76) Inventors: Robert E. Sandstrom, Longview, WA (US); Lawrence A. Crum, Bellevue, WA (US)

( * ) Notice: Subject to any disclaimer, the term of this patent is extended or adjusted under 35 U.S.C. 154(b) by 188 days.

(21) Appl. No.: 13/550,910

(22) Filed: Jul. 17, 2012

(65) Prior Publication Data

US 2012/0302884 A1  Nov. 29, 2012

Related U.S. Application Data

(63) Continuation-in-part of application No. 12/716,991, filed on Mar. 3, 2010, now abandoned.

(60) Provisional application No. 61/209,202, filed on Mar. 4, 2009.

(51) Int. Cl.
*G06K 9/00* (2006.01)

(52) U.S. Cl.
USPC .......................................... 382/131; 600/437

(58) Field of Classification Search
USPC ........... 359/327; 382/133, 134; 600/424, 427, 600/431, 437, 439, 443, 445, 447, 459; 606/7; 702/19
See application file for complete search history.

(56) References Cited

U.S. PATENT DOCUMENTS

| | | | | |
|---|---|---|---|---|
| 4,545,385 | A * | 10/1985 | Pirschel | 600/445 |
| 5,456,256 | A * | 10/1995 | Schneider et al. | 600/445 |
| 5,806,521 | A * | 9/1998 | Morimoto et al. | 600/447 |
| 6,030,377 | A * | 2/2000 | Linhares et al. | 606/7 |
| 6,661,571 | B1 * | 12/2003 | Shioda et al. | 359/372 |
| 7,018,333 | B2 * | 3/2006 | Wang et al. | 600/443 |
| 7,615,008 | B2 * | 11/2009 | Zhang et al. | 600/437 |
| 7,850,613 | B2 * | 12/2010 | Stribling | 600/459 |
| 7,885,448 | B2 * | 2/2011 | Bartels | 382/133 |
| 7,901,358 | B2 * | 3/2011 | Mehi et al. | 600/447 |
| 8,246,543 | B2 * | 8/2012 | Johnson et al. | 600/442 |
| 2004/0162486 | A1 * | 8/2004 | Stoianovici et al. | 600/427 |
| 2005/0033141 | A1 * | 2/2005 | Collins et al. | 600/407 |
| 2006/0173304 | A1 * | 8/2006 | Wang | 600/437 |
| 2006/0173307 | A1 * | 8/2006 | Amara et al. | 600/437 |
| 2006/0235300 | A1 * | 10/2006 | Weng et al. | 600/439 |
| 2007/0003989 | A1 * | 1/2007 | Ellingsen et al. | 435/7.23 |
| 2008/0033657 | A1 * | 2/2008 | Cline et al. | 702/19 |
| 2009/0030339 | A1 * | 1/2009 | Cheng et al. | 600/562 |
| 2009/0198128 | A1 * | 8/2009 | Fukutani et al. | 600/437 |

(Continued)

OTHER PUBLICATIONS

U.S. Food and Drug Administration, Information for Manufacturers Seeking Marketing Clearance of Diagnostic Ultrasound Systems and Transducers, Sep. 9, 2008, pp. 1-68.*

*Primary Examiner* — Vikkram Bali
*Assistant Examiner* — Xuemei Chen
(74) *Attorney, Agent, or Firm* — Timothy E. Siegel Patent Law, PLLC; Timothy E. Siegel

(57) ABSTRACT

A method of operating a pathology laboratory, which utilizes an ultrasound imaging device, adapted to automatically image tissue specimens, in the laboratory. Resected tissue specimens are received into the laboratory and the ultrasound imaging device is used to image some of the received tissue specimens, thereby creating 3-dimensional tissue specimen images of imaged tissue specimens. Locations on the imaged tissue specimens to take tissue sample, in order to make microscope slides, are determined in reliance on the tissue specimen images and the tissue samples are taken from the locations determined and the microscope slides are produced.

16 Claims, 4 Drawing Sheets

(56) References Cited

U.S. PATENT DOCUMENTS

| | | | |
|---|---|---|---|
| 2009/0259128 A1* | 10/2009 | Stribling | 600/459 |
| 2010/0022871 A1* | 1/2010 | De Beni et al. | 600/424 |
| 2010/0081928 A1* | 4/2010 | Hyde et al. | 600/431 |
| 2010/0183216 A1* | 7/2010 | Yamada | 382/134 |
| 2010/0286511 A1* | 11/2010 | Woerlein et al. | 600/431 |
| 2011/0040169 A1* | 2/2011 | Kamen et al. | 600/411 |
| 2011/0098566 A1* | 4/2011 | Zhang et al. | 600/443 |
| 2011/0288414 A1* | 11/2011 | Yu et al. | 600/443 |
| 2012/0089026 A1* | 4/2012 | Wang et al. | 600/443 |
| 2013/0177972 A1* | 7/2013 | Green et al. | 435/288.7 |

\* cited by examiner

METHOD OF OPERATING A PATHOLOGY LABORATORY

RELATED APPLICATION

This application is a continuation-in-part of application Ser. No. 12/716,991 filed Mar. 3, 2010 now abandoned, which is incorporated herein by reference as if fully set forth herein, and which, in turn, claims priority from provisional application Ser. No. 61/209,202, filed Mar. 4, 2009, which is also incorporated by reference as if fully set forth herein.

BACKGROUND

Pathologists typically examine tissue specimens in a laboratory setting. For each tissue specimen an initial visual inspection is made. If different types of tissue are visible, for example healthy tissue and diseased tissue, a smaller tissue sample may be taken from one or more tissue types, to permit examination under a microscope. If no tissue differentiation is immediately apparent, the pathologist will typically cut into the specimen, in search of diseased tissue. This practice is destructive to the specimen and may result in the loss of some otherwise obtainable information. For example information about the size and shape of a tumor may be lost during this process. It may also be challenging to find the diseased tissue. For example a lymph node tumor metastasis may be so small that it could be easily missed, even if several cuts are taken through a tissue specimen that includes a lymph node. Depending on the purpose of the tissue specimen examination, each microscope slide prepared may be an investment of between 5 and 20 minutes of a technician's time. The decision on which portion of the specimen to take tissue for the preparation of microscope slides determines whether or not this investment is effective, and more importantly whether the examination of the tissue specimen yields a benefit to the patient. Accordingly, it would be desirable to have some device and method to help a pathologist examine the interior of a specimen for instances of abnormal tissue, without destroying the specimen by cutting into it repeatedly.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect the present invention may take the form of a method of operating a pathology laboratory, which utilizes an ultrasound imaging device, adapted to automatically image tissue specimens, in the laboratory. Resected tissue specimens are received into the laboratory and the ultrasound imaging device is used to image some of the received tissue specimens, thereby creating 3-dimensional tissue specimen images of imaged tissue specimens. Locations on the imaged tissue specimens to take tissue samples, in order to make microscope slides, are determined in reliance on the tissue specimen images and the tissue samples are taken from the locations determined to make the microscope slides.

In a second separate aspect the present invention may take the form of a method of operating a pathology laboratory, which utilizes an ultrasound imaging device, adapted to automatically image tissue specimens, in the laboratory. Resected tissue specimens are received into the laboratory and the ultrasound imaging device is used to image some of the received tissue specimens, thereby creating 3-dimensional tissue specimen images of imaged tissue specimens. The tissue specimen images are stored on a computer and associated with information concerning the corresponding imaged tissue specimen, thereby forming a computer library of 3-dimensional tissue specimen images, and related information.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
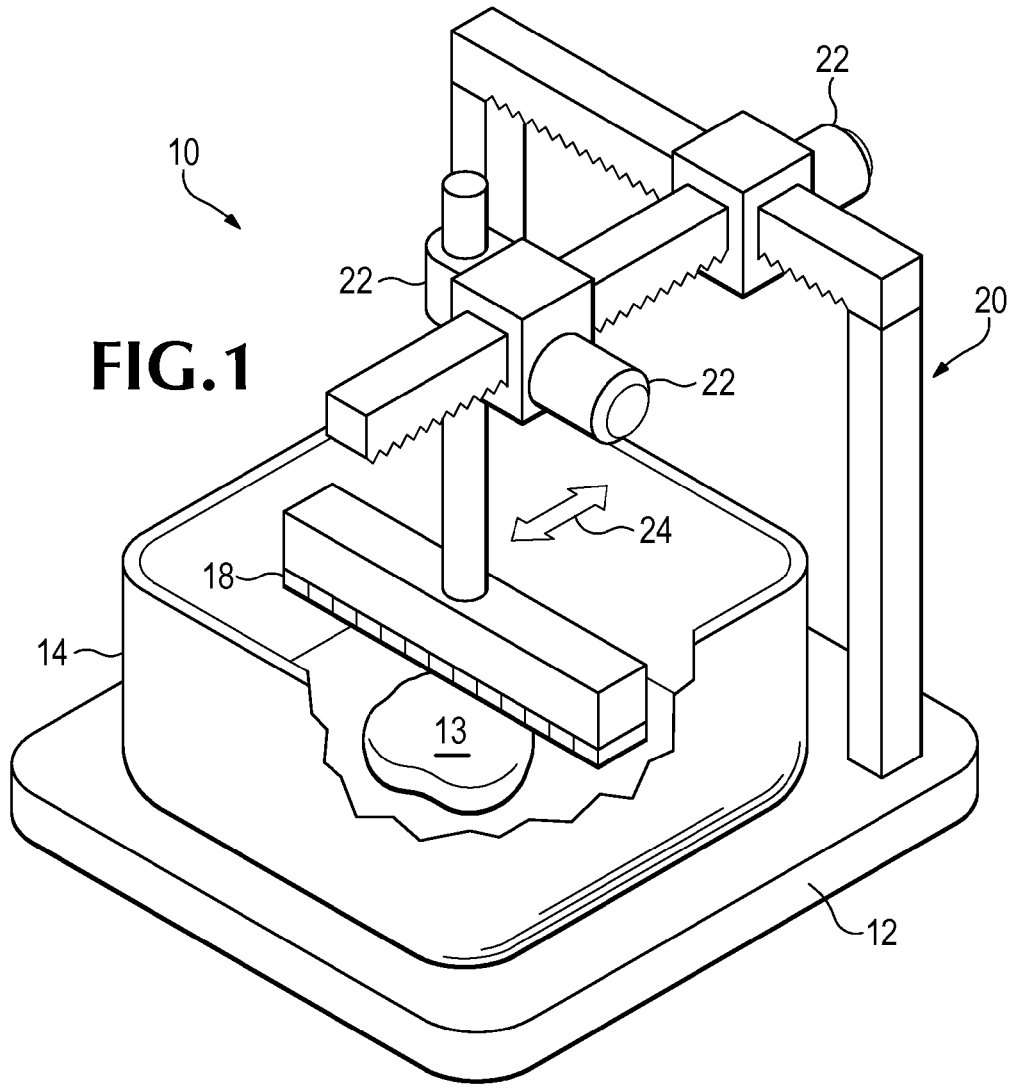
FIG. 1 is a perspective view of an imaging device according to the present invention.

A preferred embodiment of the present invention is an ultrasound imaging device 10 that can easily be supported by a flat surface, such as a laboratory countertop, and which can accept and image a tissue specimen. The device includes a base 12 supporting a container 14, in which a specimen 13 may be placed, and which may be filled with saline solution 16. A linear imaging array 18, having for example 256 piezo-electric elements is mounted on a rack system 20, that includes electric motors 22, for moving array 18 in three dimensions. In an alternative preferred embodiment a capacitive micro-machined ultrasonic transducer (CMUT) array is used. In an alternative preferred embodiment, array 18 is vertically moveable, to place it into the saline solution 16 and is moveable in the horizontal direction that is orthogonal to the length of the array 18, with resolution in the dimension along the length of the array 18 provided by electronic scanning.

In operation, the specimen 13 is placed into the bath of saline solution 16 and the array 18 is lowered, or partial enclosure 14 is raised, so that the lower portion of array 18 is immersed in the saline solution 16. This reduces boundary and low-transmission effects, as the boundary between saline solution and a tissue specimen is typically not as reflective as the boundary between air and a tissue specimen. In an alternative embodiment the partial enclosure 14 is filled with a biocompatible gel, into which the tissue specimen 13 is placed. In yet another preferred embodiment the array 18 is brought into contact with the specimen 13, either with the assistance of a human operator or automatically by a system that includes sufficient sensing and intelligence to bring the probe into contact with the tissue specimen 13, without harming or significantly distorting the tissue specimen 13. In one preferred embodiment, the array 18 is covered by an ultrasound substantially transparent material, to protect it. The linear piezoelectric array is scanned past the specimen 13 in a first dimension 24 (FIG. 1), imaging as it scans.

Although the electrical connections are not shown in the physical drawings provided herein, as is well known in the art, the piezoelectric elements of array 18 are electrically driven to produce a sound signal having a wavelength in the 85-770 micron range (2-18 MHz).

Because the tissue specimen has been removed from the patient's body, the power levels to which it can be subjected are greatly eased, thereby potentially leading to far superior imaging results. Nevertheless, there is still a cost to thermally or mechanically damaging tissue characteristics prior to microscope examination of the tissue specimen. In one preferred embodiment, the intensity of the sound field is controlled to be greater than about 50 mW/cm$^2$ (spacial peak, temporal average [SpTa]) so as to give good resolution. In a preferred embodiment the SpTa power may be raised briefly to above 1.5 W/cm$^2$ in order to gain fine resolution of the tissue specimen as a whole, or a portion thereof. In alternative preferred embodiments, SpTa power may exceed 1.2 W/cm$^2$, 1 W/cm$^2$ and 0.8 W/cm$^2$. In one preferred embodiment this control is performed automatically, but in another user controls permit a technician to adjust the sound intensity to effect optimal sound power levels.

Figure 3:
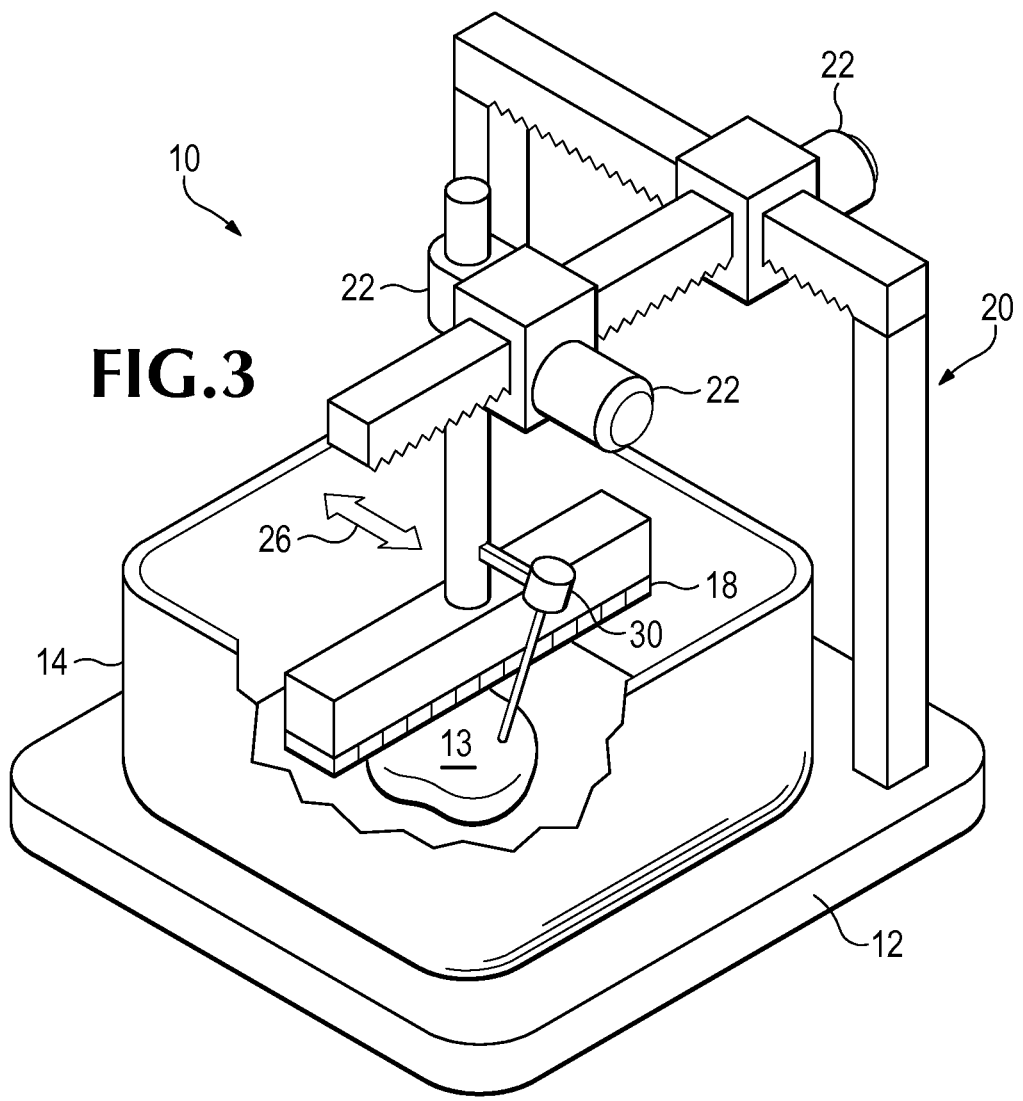
FIG. 3 is a perspective view of an imaging device similar to that of FIG. 1, with the imaging head turned relative to its position in FIG. 1 and including a robot arm.

The sound waves travel through the specimen 13 until reflected by some change in tissue quality. Container 14 is made of a material that is highly absorptive to ultrasound waves and is as unreflective of ultrasound waves as possible. After transmitting, array 18 is switched to receive mode and the timing of the received ultrasound signals indicates the depth into tissue specimen 13 at which the ultrasound waves were reflected. Array 18 may be electrically focused to form a beam that is scanned in dimension 26 (FIG. 3), for the configuration shown in FIG. 1. Accordingly, at each position of array 18, a two-dimensional slice of data into the specimen can be found by a data processing assembly (not shown). The dimensions are depth, into the specimen, and dimension 26 (see FIG. 3). In one preferred embodiment, a mechanical scan in only dimension 24 is performed, with the electronic scanning providing resolution in dimension 26. But in an additional preferred embodiment, as shown in FIG. 3, array 18 is rotated by 90° and is scanned across specimen 13 along dimension 26, with high resolution cells formed in dimension 24. The two scans are reconciled by the data processing assembly to arrive at a high resolution 3-dimensional image. In this embodiment, ensuring that the specimen does not move or is displaced or distorted between the two scans is important. Accordingly, in one preferred embodiment anti-vibration technology is used to cancel any vibrations that would otherwise change the position of specimen 13. In one preferred embodiment, structure 20 is mounted separately from base 12, so that vibrations from the movement of array 18 are further isolated from specimen 13.

Figure 2:
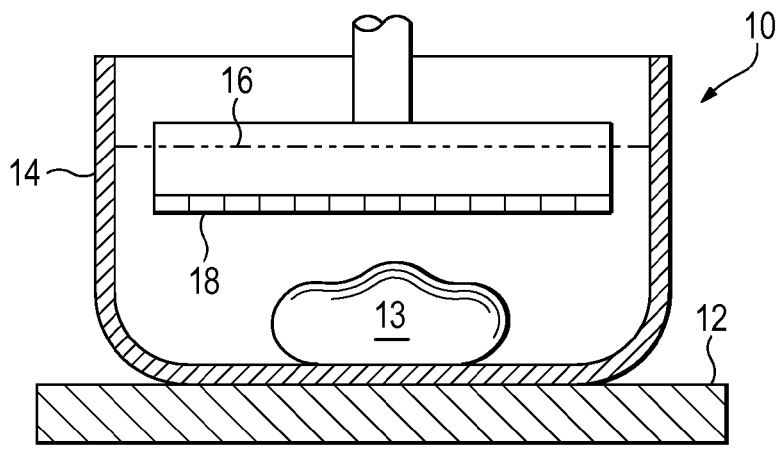
FIG. 2 is a side elevation sectional view of the imaging device of FIG. 1.

The embodiment of FIGS. 1 and 2, as well as other embodiments disclosed, are very helpful in finding foreign bodies within a tissue specimen, particularly when used near the surgical theater. A surgeon may have difficulty determining if an entire foreign body has been removed. If he can see the foreign body in an image of the tissue specimen then this can help him assess the extent to which his efforts to remove a foreign body have been successful.

FIG. 3 also shows robotic arm 30, which can be remotely guided, and used to place a marker in the form of dye, or a metal or plastic clip into specimen 13 to indicate to a lab technician where to take a section. In an alternative preferred embodiment, a person may manually place such a marker.

Figure 4:
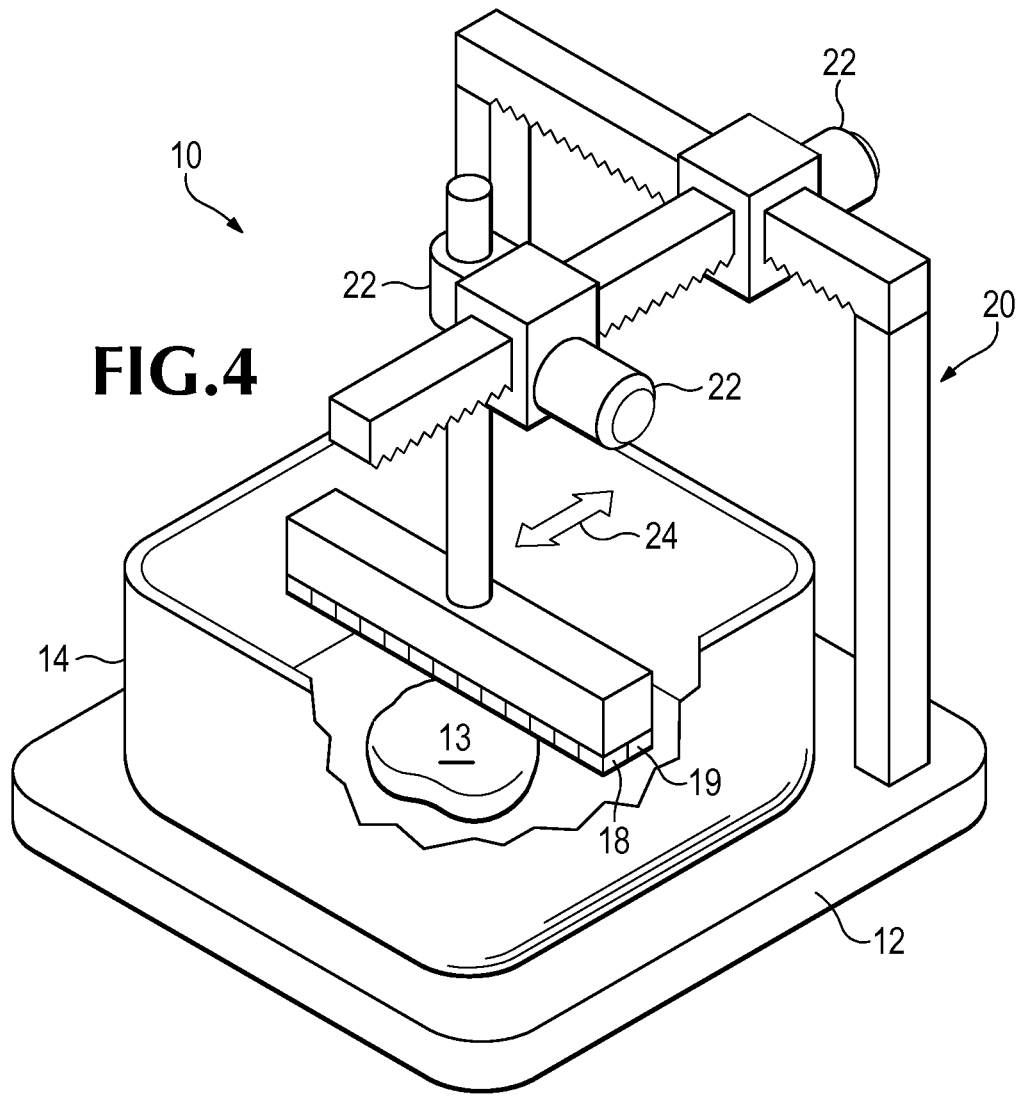
FIG. 4 is a perspective view of an alternative embodiment of an imaging device, having two transducer arrays.

As shown in FIG. 4, an additional transducer array 19, is held on the same assembly as array 18. Array 19 is tuned to transmit and receive at a center frequency of between 18 MHz to 60 MHz (wavelength: approximately 25 to 85 microns), depending on the preferred embodiment implemented. The choice of frequency involves a tradeoff between resolution, which is roughly equal to wavelength, and depth of imaging required. Tissue specimen size is dependent on the purpose of specimen examination and the circumstances under which the tissue specimen is taken. A 50 MHz sound wave can penetrate to a depth of about 1 cm, which may be adequate under many circumstances, but for other tissue specimens a deeper penetration could be highly desirable. On the other hand, some tissue conditions which would suggest a closer examination are evident at the 100 micron resolution range, whereas other conditions require a resolution closer to the size of many human tissue cells, which is in the range of about 5-20 microns. In some cases the specimen will be moved before being imaged with higher resolution array 19. The surfaces of the specimen may be of particular importance in assessing the patient condition as in some instances the specimen will have been generated in an effort to remove a tumor. In this situation, the surface condition may provide an indication as to the complete removal of the tumor. Accordingly, after a first, initial assessment imaging, the specimen can be oriented so that the surface area of greatest interest can be closely examined.

Figure 5:
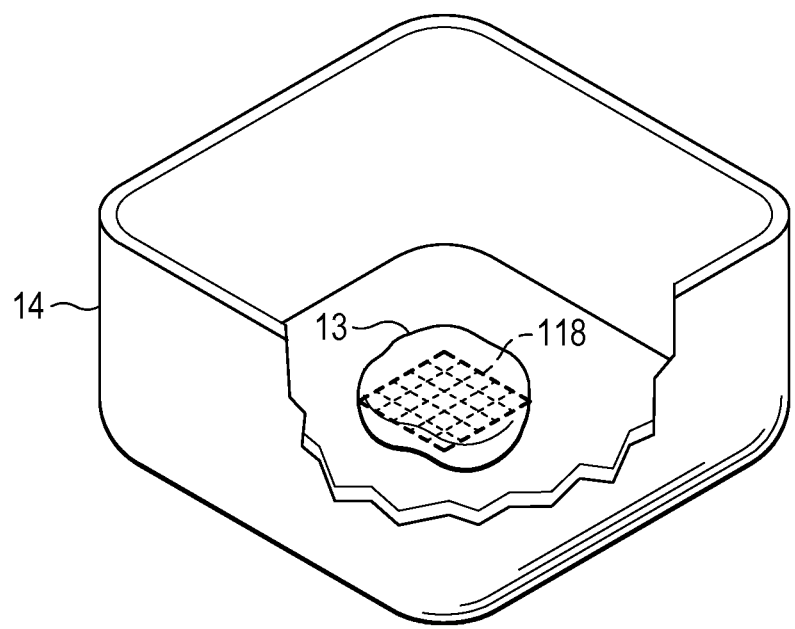
FIG. 5 is a top perspective view of an alternative embodiment of an imaging device according to the present invention, having a two-dimensional ultrasound transducer placed below a tissue specimen.

Referring to FIG. 5, in an additional preferred embodiment, a two-dimensional piezoelectric array 118 is used, to form a beam that is narrow and steerable in two orthogonal dimensions. This beam is scanned over the specimen to form a 3-dimensional image, in the two orthogonal dimensions and in range (in other words depth into the specimen). As array 118 does not need to be moved, it may be placed as shown, into the bottom of container 14. Array 118 may be a piezoelectric transceiver or a capacitive micro-machined ultrasonic transducer (CMUT). In one preferred embodiment the specimen is held above the floor of container 14, to give the beam coverage volume from array 118 room to spread out.

In another preferred embodiment, the beam is electronically scanned in one dimension and mechanically scanned in the other, without the second scan shown in FIG. 3. In this embodiment there are many more elements along the dimension that is electrically scanned, and to improve resolution in the mechanically scanned dimension between 3 and 20 elements, which are not electrically steerable, but are fixed in relative intensity to form a beam that is narrower in the horizontally scanned dimension. In another embodiment, the array is essentially square and is electronically scanned in both dimensions. In another preferred embodiment x-rays or infrared light is used, either in conjunction with ultrasound to form a more certain image, or instead of ultrasound. In one preferred method a hand held ultrasound device is used to form an image of a tissue specimen.

In a preferred embodiment, the imaging device 10 includes a low frequency head and a high frequency head. The low frequency head may be used to form an initial image, with the high frequency head being used to gain a higher resolution image of any areas of interest revealed by the scan with the low frequency head and/or to image the surfaces of the tissue specimen 13, as high frequency ultrasound does not penetrate as far into a tissue specimen as low frequency ultrasound of the same power.

Additionally, the device 10 provides or supports data and image storage. In one preferred embodiment, the device 10 is adapted to be connected to a computer where images can be stored. In another preferred embodiment device 10 includes its own data and image storage device. One great advantage of these embodiments is that before the pathologist cuts into a specimen, thereby partially destroying it, an image set of a specimen feature can be made and stored for future reference. In a preferred embodiment, it is possible to enter additional data into the image. For example, after the pathologist has determined tissue type for a feature apparent in the image formed by device 10, he can associate this tissue type with the feature. In one preferred embodiment, various tissue types can be assigned differing false colors or other indicating characteristics, so that a 3-dimensional map of the specimen can be created.

Figure 6:
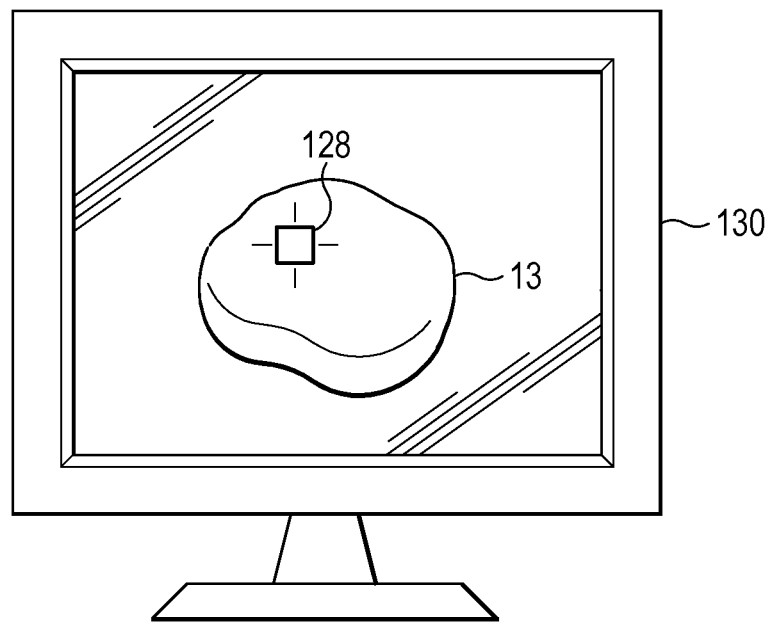
FIG. 6 is a front elevational view of a display forming a part of an imaging assembly according to the present invention, showing a tissue specimen, having a location marked.

Referring to FIG. 6, in another preferred embodiment a first health care provider, for example a pathologist, can indicate where to collect tissue sections for microscopic examination, from the specimen, by creating a mark 128 on an electronically displayed three-dimensional image 130 of specimen 13 with a mouse or a computer screen pen. In the context of this application the term "three-dimensional image" includes a two-dimensional image that imparts information about a three-dimensional volume, by perspective and shading. In one embodiment, however, stereoscopic techniques are used to present a truly three-dimensional image to the user. After microscopic imagery has been formed of the tissue sections, it may be related back to the three dimensional imagery, so that a viewer could see the microscopic imagery and at the same time see where in the tissue specimen the tissue section shown in the microscopic imagery originated.

A preferred embodiment includes computer software and a display screen, either integral with device 10, or on a lap top communicatively connected to device 10, where the data collected from the ultrasound imaging process can be stored and later augmented by the pathologist or technician, in reliance on the microscope imagery obtained through the further microscope examination. The software is also capable of displaying mammogram, computer aided tomography (CAT), other x-ray, positron emission tomography (PET), magnetic resonance imaging (MRI) or ultrasound in vivo pre-operation or intra-operation imagery in tandem with the imagery of the resected tissue specimen. This imagery may also be made available to the attending physician, to see the tissue specimen information in the context of the patient's body, to inform the medical decision as to the status of the patient's medical condition. In one preferred embodiment a user can mark on the in vivo imagery the place where the resected tissue specimen was taken and cause the resected tissue specimen imagery to be placed at that location, to form a composite image of the original bodily condition in that region and facilitate the medical decision makers' efforts to gain a complete view of the patient's medical condition.

In one method, a lab technician runs specimens through device 10 as they come into the laboratory and then a pathologist looks through a set of images marking them for section taking and slide fixing. The technician takes the sections and forms a microscopic image, which is then associated with the image of the specimen 13 with, for example, a line connecting the microscope image to the place on the specimen where the section was taken. The pathologist may then copy the image and mark places on the specimen where it appears to him that the same tissue type may exist. Skilled persons will readily recognize that this method generally does not include the imaging of every single specimen arriving at the laboratory, but rather only those specimens from which the laboratory decision maker(s) expect that a benefit could be gained from such imaging.

In another preferred embodiment, software associated with device 10 creates a folder for storage of all information relating to the tissue sample, so that imaging samples and all other information, such as images of microscopic examination of further specimens taken from the tissue specimen, may be stored together and retrieved together. In a variant of this embodiment, a bar code is assigned to this electronic folder, so that a bar code sticker may be placed on a paper file or other physical item, so that a simple scan will retrieve the electronic folder. The identifying bar code (the term bar code is inclusive of any computer readable code, including an RFID chip) may be placed on the specimen container at the time the specimen is collected and associated at that time with the patient. In one preferred embodiment the health care professional collecting and/or handling the tissue sample, enters patient identifying data into a device which prints out a bar code indicating a particular patient, the date and time of specimen collection and any other relevant data concerning the specimen.

Additionally, differences in tissue reflectivity can be highlighted to indicate to an image viewer the location of potential areas of pathology in the tissue specimen. In particular, significant advances have been made recently in the use of ultrasound for tissue characterization. Thus, in many cases, the ultrasound itself can be used to identify regions of interest to the examiner that would not be possible by visual examination alone. This ability to use ultrasound as a unique probe of the characteristics of tissue could be particularly useful for finding very small tumors, for example in the examination of lymph nodes for tumor.

Device 10 may also be used in a surgical setting. During surgery it may be critically important to quickly gain an understanding of the ultrasonic characteristics of any excised lesion. For example, when a tumor is removed, it may be quite difficult to determine if any part of the tumor has been left in the body. By ultrasonically examining the resection (removed tissue), it may be possible to determine if the tumor extends to the surgical margin (the edge of the removed tissue). If it does, then it is likely that the tumor was cut through in the resection, indicating that a portion of the tumor may still be in the patient. Those skilled in the surgical arts are likely to recognize other applications for a penetrating imaging device, located near or in the surgical theater. A preferred embodiment is sized to image tissue specimens ranging from less than 1 square cm, to the size of an organ, such as the spleen or a kidney.

In one preferred embodiment of a tissue specimen ultrasound device, a powered train of containers is provided so that a technician can load a number of specimens at the same time, and the specimens will be brought under the array 18 one at a time, for imaging. A bar code reader or RFID reader is used to read the identity of the specimens from the bar code or RFID chip that has accompanied the container from a health care provider.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of operating a pathology laboratory, comprising:
   (a) providing an ultrasound imaging device, adapted to automatically image tissue specimens, in said laboratory;
   (b) receiving resected tissue specimens into said laboratory;
   (c) using said ultrasound imaging device to image some of said received tissue specimens, thereby creating 3-dimensional tissue specimen images of imaged tissue specimens;
   (d) determining locations on said imaged tissue specimens to take tissue samples in order to make microscope slides, in reliance on said tissue specimen images; and
   (e) taking said tissue samples from said locations determined and making said microscope slides.

2. The method of claim 1, wherein said locations on said imaged tissue specimens are marked directly on said tissue specimens.

3. The method of claim 2, wherein said locations are marked on each said tissue specimen by inserting physical markers into said tissue specimen.

4. The method of claim 2, wherein said locations are marked on each said tissue specimens by injecting dye into said tissue specimen.

5. The method of claim 1, wherein said tissue specimens are first imaged at a first ultrasound frequency, and wherein some of said imaged tissue specimens are subsequently imaged at a second ultrasound frequency at least twice as high as said first ultrasound frequency, to provide higher resolution imagery.

6. The method of claim 5, wherein said first frequency differs in dependence on said tissue specimen.

7. The method of claim 1, wherein some tissue specimens are subjected to ultrasound power in excess of 0.8 W/cm$^2$ on a spatial peak, temporal average (SpTa) basis.

8. The method of claim 7, wherein some tissue specimens are subjected to ultrasound power in excess of 1 W/cm$^2$ SpTa.

9. The method of claim 8, wherein some tissue specimens are subjected to ultrasound power in excess of 1.2 W/cm$^2$ SpTa.

10. The method of claim 9, wherein some tissue specimens are subjected to ultrasound power in excess of 1.5 W/cm$^2$ SpTa.

11. A method of operating a pathology laboratory, comprising:
    (a) providing an ultrasound imaging device, adapted to automatically image tissue specimens, in said laboratory;
    (b) receiving resected tissue specimens into said laboratory;
    (c) using said ultrasound imaging device to image some of said received tissue specimens, thereby creating 3-dimensional tissue specimen images of imaged tissue specimens;
    (d) determining locations on said imaged tissue specimens to take tissue samples in order to make microscope slides, in reliance on said tissue specimen images; and
    (e) storing each said imaged tissue specimen image on a computer and associating said image with information concerning said corresponding imaged tissue specimen, thereby forming a computer library of 3-dimensional tissue specimen images, associated to related information.

12. The method of claim 11, wherein said imaged tissue specimens are destroyed, at some time after imaging.

13. The method of claim 11, further including microscope imaging of tissue samples taken from said tissue specimens, thereby forming tissue sample microscope images, from at least some of said imaged tissue specimens.

14. The method of claim 13, wherein said tissue sample microscope images from a said tissue specimen are associated with said 3-dimensional tissue specimen image, from said tissue specimen, on said computer.

15. The method of claim 14, wherein said sample microscope images are each associated to the location on said tissue specimen image from which said tissue sample was taken, on said computer.

16. The method of claim 11, wherein said resected tissue specimens are formed by resecting tissue specimens from patients' bodies and wherein for at least some of said resected tissue specimens, in vivo imagery of the environment from which said tissue specimen is resected is formed prior to said resection and wherein said imaged resected tissue specimen image is displayed in tandem with said in vivo imagery.

* * * * *